United States Patent [19]
Odell et al.

[11] Patent Number: 5,811,249
[45] Date of Patent: Sep. 22, 1998

[54] CONTROL OF INFECTIOUS MICROORGANISMS BY MODULATION OF CHORIONIC GONADOTROPIN-RELATED PROTEIN ACTIVITY

[75] Inventors: William D. Odell, Salt Lake City; Jeanine T. Griffin, Holladay; Omar Caticha, Salt Lake City, all of Utah

[73] Assignee: University of Utah Research Foundation, Salt Lake City, Utah

[21] Appl. No.: 327,362

[22] Filed: Oct. 21, 1994

[51] Int. Cl.⁶ .............................. G01N 33/53; C07K 16/14
[52] U.S. Cl. .................. 435/7.31; 435/72; 530/388.5; 530/388.1
[58] Field of Search .................................. 435/7.31, 7.2; 530/388.5, 388.1

[56] References Cited

U.S. PATENT DOCUMENTS

| | | | |
|---|---|---|---|
| 4,182,753 | 1/1980 | Saltarelli | 424/115 |
| 4,508,643 | 4/1985 | Calamai et al. | 260/112 |

OTHER PUBLICATIONS

O.S. Kinsman et al., *Effect of Mammalian Steroid Hormones and Luteinizing Hormone on the Germination of Candida albicans and Implications for Vaginal Candidosis*, 31 Mycoses 617 (1988).

F.C. Odds, Morphogenesis in Candida with special reference to *Candida albicans*, in Candida and *Candidosis* 42–59 (1988).

David R. Soll, Dimorphism and high–frequency switching in *Candida albicans*, in The Genetics of Candida 147–176 (D.R. Kirsch, R. Kelly, M.B. Kurtz eds., 1990).

K.C. Hazen & J.E. Cutler, *Autoregulation of Germ Tube Formation by Candida albicans*, 24 Infect. Immun. 661 (1979).

O. Caticha et al., *Stimulation of Candida Albicans Transition by Human Chorionic Gonadotropin and a Bacterial Protein*, 18 Endocr. Res. 133 (1992).

T.A. Bramley et al., *Specific, High Affinity Binding Sites for Human Luteinizing Hormone and Human Chorionic Gonadotrophin in Candida Species*, 167 Biochem. Biophys. Res. Commun. 1050 (1990).

S. Grover et al., *Isolation of a 48.5 kDa Membrane Protein for Pseudomonas maltophilia which Exhibits Immunologic Cross–Reaction to the β–Subunit of Human Chorionic Gonadotropin*, 128 Endocrinology 3096 (1991).

D.T. Carrell & W.D. Odell, *A Bacterial Binding Site Which Binds Human Chorionic Gonadotrophin but Not Human Luteinizing Hormone*, 18 Endocr. Res. 51 (1992).

O. Caticha et al., *Characterization of a human chorionic gonadotrophin–like protein from Candida albicans*, 132 Endocrinology 667 (1993).

J. Griffin & W.D. Odell, *Ultrasensitive immunoradiometric assay for chorionic gonadotrophin which does not react with luteinizing hormone nor free beta–chain of hCG and which detects hCG in blood of nonpregnant humans*, 103 J. Immunol. Methods 275 (1987).

S. Grover et al., *Ultrasensitive, specific, two–antibody immunoradiometric assay that detects free alpha subunits of glycoprotein hormones in blood of nonpregnant humans*, 37 Clin. Chem. 2069 (1991).

W. Odell et al., *Two–monoclonal–antibody sandwich–type assay for thyrotropin, with use of an avidin–biotin separation technique*, 32 Clin. Chem. 1873 (1986).

S. Grover et al., *Isolation of a 30 kDa mmunoglobulin Biding Protein from Pseudomonas maltophilia*, 141 J. Immunol. Methods 187 (1991).

D. Carrell & W. Odell, *A bacterial binding site which binds human chorionic gonadotropin but not human luteinizing hormone*, 18 Endocrine Res. 51 (1992).

O. Caticha et al., *An anti–human chorionic gonadotrophin (HCG) monoclonal antibody inhibits Candida albicans transition in vitro and prevents infection in vivo*, 42 Clin. Res. 287A (1994) (abstr.).

S. Grover et al., *Partial nucleotide sequence of the Xanthomonas maltophilia chorionic gonadotropin–like receptor*, 190 Biochem. Biophys. Res. Commun. 371 (1993).

D.T. Carrell et al., *Evidence for an autocrine/paracrine function of chorionic gonadotropin in Xanthomonas maltophilia*, 132 Endocrinology 1085 (1993).

Primary Examiner—Susan A. Loring
Attorney, Agent, or Firm—Thorpe, North & Western, L.L.P.

[57] ABSTRACT

A method of controlling, in a warm-blooded animal, an infectious microorganism expressing a chorionic gonadotropin-like growth-regulating protein comprises modulating the activity of the protein by administering to the warm-blooded animal an effective amount of an antibody capable of inhibiting the activity of the protein, the chorionic gonadotropin-like growth-regulating protein itself such that the animal develops a neutralizing immune response, or peptides that block the receptors of the chorionic gonadotropin-like growth-regulating protein in the infectious microorganism. *Candida albicans* is one such microorganism that can be controlled by delivering an antibody against the growth-regulating protein, CaCGLP. Mycobacteria can also be controlled by this method. A method of inhibiting transition of *Candida albicans* blastospores in vitro by contacting the blastospores with an antibody against CaCGLP is also disclosed. A method of inhibiting growth of mycobacteria in vitro comprises contacting the mycobacteria with an antibody against an endogenous chorionic gonadotropin-like growth-regulating protein. In vitro growth of microorganisms can also be stimulated by contacting the microorganism with a chorionic gonadotropin-like growth-regulating protein.

2 Claims, 8 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 93 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Mycobacterium vaccae
        ( B ) STRAIN: ATCC 15483

( x i ) SEQUENCE DESCRIPTION: SEQ ID NO:1:

```
Ile Leu Gln Asp Leu Arg Gly Pro Pro Val Gly Tyr Lys Asp Ile Arg
 1               5                  10                  15

Leu Asp Pro Val Gly Ser Ile Arg Met Cys Gly Val Pro Val Pro Ser
                20                  25                  30

Arg Cys Pro Trp Pro Leu Cys Arg Arg Ile His Arg Gln Ala Ala Arg
            35                  40                  45
```

His Val Asp His Ala Leu Gly Gln Phe Arg Ala Pro Pro Leu Ala Leu
50                      55                      60

Ala Ala Ser Thr Ala Leu Lys Ser Arg Ser Asn Pro Glu Gly Asn Asp
65                  70                  75                      80

Arg Cys Thr Ala Arg Arg Cys Ser Arg Ala Pro Cys Pro
                85                  90

( 2 ) INFORMATION FOR SEQ ID NO:2:

( i ) SEQUENCE CHARACTERISTICS:
    ( A ) LENGTH: 88 amino acids
    ( B ) TYPE: amino acid
    ( D ) TOPOLOGY: linear ( i i ) MOLECULE TYPE: protein ( v i ) ORIGINAL SOURCE:
    ( A ) ORGANISM: Homo sapiens ( x i ) SEQUENCE DESCRIPTION: SEQ ID NO:2:

Leu Pro Gln Val Val Cys Asn Tyr Arg Asp Val Arg Phe Glu Ser Ile
1               5                   10                  15

Arg Leu Pro Gly Cys Pro Arg Gly Val Asn Pro Val Val Ser Tyr Ala
                20                  25                  30

Val Ala Leu Ser Cys Gln Cys Ala Leu Cys Arg Arg Ser Thr Thr Asp
            35                  40                  45

Cys Gly Gly Pro Lys Asp His Pro Leu Thr Cys Asp Asp Pro Arg Phe
    50                  55                  60

Gln Asp Ser Ser Ser Ser Lys Ala Pro Pro Pro Ser Leu Pro Ser Pro
65                  70                  75                      80

Ser Arg Leu Pro Gly Pro Ser Asp
                85

( 2 ) INFORMATION FOR SEQ ID NO:3:

( i ) SEQUENCE CHARACTERISTICS:
    ( A ) LENGTH: 78 amino acids
    ( B ) TYPE: amino acid
    ( D ) TOPOLOGY: linear ( i i ) MOLECULE TYPE: protein ( v i ) ORIGINAL SOURCE:
    ( A ) ORGANISM: Xanthomonas maltophilia
    ( B ) STRAIN: ATCC 13637

( x i ) SEQUENCE DESCRIPTION: SEQ ID NO:3:

Leu His Asp Val Met Tyr Lys Asp Ile Arg Phe Gly Glu Ser Ile Arg
1               5                   10                  15

Ser Arg Met Cys Pro Arg Cys Val Lys Pro Val Pro Ser Pro Thr Ala
                20                  25                  30

Pro Pro Ala Gly Leu Ala Ala Phe Ser Asn Arg Arg Thr Glu Arg Cys
            35                  40                  45

Leu Val Trp Ile Ala Cys Val His Arg Leu Ser Ala Val Gly Glu Ala
    50                  55                  60

Gly Ser Leu Asn Glu Pro Glu Ala Ala Arg Leu Ala Asn Asp
65                  70                  75

( 2 ) INFORMATION FOR SEQ ID NO:4:

( i ) SEQUENCE CHARACTERISTICS:
    ( A ) LENGTH: 20 base pairs
    ( B ) TYPE: nucleic acid (C) STRANDEDNESS: single
(D) TOPOLOGY: linear (xi) SEQUENCE DESCRIPTION: SEQ ID NO:4:

CAGACTTTTG CATGGGGCTC　　　　　　　　　　　　　　　　　　　　　　20

(2) INFORMATION FOR SEQ ID NO:5:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:5:

ATCGGTGAAG ATGAGGATTG C　　　　　　　　　　　　　　　　　　　　　21

CONTROL OF INFECTIOUS MICROORGANISMS BY MODULATION OF CHORIONIC GONADOTROPIN-RELATED PROTEIN ACTIVITY

BACKGROUND OF THE INVENTION

This invention was made with government support under Grant No. 1R55DK44900-01 awarded by the National Institute of CHD. The government has certain rights in the invention.

This invention relates to a method of controlling growth of microorganisms. More particularly, this invention relates to a method of controlling growth of fungi, such as *Candida albicans*, and bacteria, such as mycobacteria and xanthomonads, by modulating the activity of an endogenous chorionic gonadotropin-related protein produced by such microorganisms.

Candida is a genus of imperfect fungi characterized by two principal growth habits, yeast cells (or blastospores) and hyphae (or mycelia). It is the only fungus that is commonly part of the normal flora of the skin, mouth, intestinal tract, and vagina, but can cause a variety of infections, including candidiasis, onychomycosis, tinea corporis, tinea pedis, vaginitis, and thrush. *C. albicans* is the usual pathogen, but other species may also cause infection. Candidiasis is usually a superficial infection of the moist cutaneous areas of the body and most commonly involves the skin, oral mucous membranes, respiratory tract, and vagina. Rarely, there is a systemic infection or endocarditis. Pregnancy predisposes women to infection by *C. albicans*. E.g., O. S. Kinsman et al., *Effect of Mammalian Steroid Hormones and Luteinizing Hormone on the Germination of Candida albicans and Implications for Vaginal Candidosis*, 31 Mycoses 617 (1988). Opportunistic infections have become increasingly frequent with the expanding population of immunocompromised individuals.

Hyphal or mycelial forms of *Candida albicans* are more associated with pathogenicity in humans and animal models than the yeast forms. F. C. Odds, *Morphogenesis in Candida with special reference to Candida albicans, in Candida and Candidosis* 22–61 (1988). The mycelial form is invariably seen in smears, scrapings, or histological sections from lesions due to *C. albicans*, and blastospores produce mycelium in tissues within hours of inoculation into experimental animals. Little is known about the biochemical and molecular basis of the transition of *C. albicans* from yeast to hyphae, and genes unique to either of the forms have not yet been isolated. M. B. Kurtz, *Dimorphism and high-frequency switching in Candida albicans, in The Genetics of Candida* 57–75 (D. R. Kirsch, R. Kelly, M. B. Kurtz eds., 1990). However, environmental changes are well known to influence transition in *C. albicans*, and several enhancers and inhibitors of transition have already been described. F. C. Odds, *Morphogenesis in Candida with special reference to Candida albicans, in Candida and Candidosis* 22–61 (1988). Of particular interest is a description of an autoregulatory substance produced by *C. albicans*, called morphogenic autoregulatory substance, produced by cultures of high concentrations of yeast ($10^8$ yeast/ml), and reported to inhibit transition in *C. albicans*. K. C. Hazen & J. E. Cutler, *Autoregulation of Germ Tube Formation by Candida albicans*, 24 Infect. Immun. 661 (1979). This substance has not been characterized biochemically and only its activity in culture media was described.

A resurgence in the frequency of occurrence of tuberculosis has occurred in recent years, especially among persons with weakened immune systems. Tuberculosis has become one of the major opportunistic infections plaguing patients with acquired immune deficiency syndrome (AIDS). Tuberculosis is caused by species of Mycobacterium, principally *M. tuberculosis*. Drug-resistant strains have appeared recently, making treatment very difficult.

Human chorionic gonadotropin (hCG) and human luteinizing hormone (hLH) are glycoprotein hormones from a family also containing human follicle stimulating hormone (hFSH) and human thyroid stimulating hormone (hTSH). These hormones are composed of common α-subunits and unique β-subunits. For example, the β-subunits of hCG and hLH differ by the presence of a 31 amino acid carboxyl-terminal ("carboxyl-tail") region in hCG that is absent in hLH, but have 80% amino acid sequence identity in the remainder of the β-subunit. Recently, the effects of human chorionic gonadotropin (hCG), human luteinizing hormone (hLH), and an hCG-like protein (xCG) isolated from *Xanthomonas maltophilia* have been described on transition in *C. albicans*. O Caticha et al., *Stimulation of Candida Albicans Transition by Human Chorionic Gonadotropin and a Bacterial Protein*, 18 Endocr. Res. 133 (1992). All three proteins stimulated transition with a minimal dose of 100 ng/ml, and also bound with high affinity nanomolar $K_d$s to *C. albicans* blastospores. Specific hCG and hLH binding, as well as the effects of hLH and steroids in the transition of *C. albicans*, have also been previously published. T. A. Bramley et al., *Specific, High Affinity Binding Sites for Human Luteinizing Hormone and Human Chorionic Gonadotrophin in Candida Species*, 167 Biochem. Biophys. Res. Commun. 1050 (1990); O. S. Kinsman et al., *Effect of Mammalian Steroid Hormones and Luteinizing Hormone on the Germination of Candida Albicans and Implications for Vaginal Candidosis*, 31 Mycoses 617 (1988). An immunologic cross-reaction is exhibited between the 48.5 kD xCG protein and the β-subunit of hCG. S. Grover et al., *Isolation of a 48.5 kDa Membrane Protein for Pseudomonas maltophilia which Exhibits Immunologic Cross-Reaction to the β-Subunit of Human Chorionic Gonadotropin*, 128 Endocrinology 3096 (1991). When added to cultured *X. maltophilia*, xCG causes a dose-dependent change in both the morphology of the bacteria and the cell density at the stationary stage of the growth cycle. The same bacteria possess a surface binding site that binds hCG, but not hLH, D. T. Carrell & W. D. Odell, *A Bacterial Binding Site Which Binds Human Chorionic Gonadotrophin but Not Human Luteinizing Hormone*, 18 Endocr. Res. 51 (1992). This site is the only known high affinity binding site in nature that distinguishes hCG from hLH. More recently, an hCG-like protein has been characterized from *C. albicans*. O. Caticha et al., *Characterization of a human chorionic gonadotropin-like protein from Candida albicans*, 132 Endocrinology 667 (1993). This 68 kD protein, termed *Candida albicans* chorionic gonadotropin-like protein (CaCGLP), appears to be a potent inducer of transition. It is presumed to represent an endogenous transition-inducing substance. This protein reacted with the following hCG immunoassays: a polyclonal rabbit anti-hCG equilibrium assay, a carboxy-tail hCG equilibrium assay, two hCG equilibrium assays using monoclonal antibodies, a free α-subunit equilibrium assay using a monoclonal antibody, and an ultrasensitive immunoradiometric assay for hCG that does not cross-react with hLH or the free β-subunit of hCG. In a specific hLH immunoradiometric assay, however, CaCGLP showed no reaction. When CaCGLP was tested in a transition assay containing 4% rat serum, the protein was 100-fold more potent than hCG in producing transition in *C. albicans*.

CG-like substances have also been found using immunological methods on the surface of strains of Streptococcus species (ATCC 12818), Staphylococcus species (ATCC 19433, 27848), *Enterococcus coli* (*E. coli*, ATCC 25922), and *X. maltophilia* (ATCC 13637) in efforts to establish a link between human cancers and the production of CG-like substances by bacteria, since these bacteria were obtained from patients with cancer.

In view of the foregoing, it will be appreciated that a method of controlling growth of microorganisms by modulating the activity of a growth-regulating CG-like protein produced by these microorganisms would be a significant advancement in the art.

OBJECTS AND SUMMARY OF THE INVENTION

It is an object of the present invention to provide a method of controlling transition of *Candida albicans* from yeast to hyphae in vitro.

It is also an object of the invention to provide a method of treating fungal infections by *Candida albicans* in warm-blooded animals including humans.

It is another object of the invention to provide a method of controlling growth of mycobacteria in vitro.

It is a further object of the invention to provide a method of treating mycobacterial infections in warm-blooded animals including humans.

It is a still another object of the invention to provide a method of controlling growth of a microorganism that produces a growth-regulating chorionic gonadotropin-like protein.

These and other objects may be accomplished by a method of controlling, in a warm-blooded animal, an infectious microorganism expressing a chorionic gonadotropin-like growth-regulating protein. The method comprises delivering to the warm-blooded animal an effective amount of an immunotherapy agent that is capable of inhibiting the activity of the protein. Infectious microorganisms from the fungal genus Candida and the bacterial genus Mycobacterium are susceptible to control by this method. The fungus *Candida albicans* is controlled by delivering a monoclonal antibody against the growth regulating protein, CaCGLP. The monoclonal antibody is directed toward an hCG-specific epitope on the body of βhCG-subunit. Immunotherapy agents, such as monoclonal antibodies, can be delivered by systemic administration.

A method of inhibiting transition of *Candida albicans* blastospores in vitro comprises providing an immunotherapy agent capable of inhibiting the activity of CaCGLP and contacting the blastospores with the immunotherapy agent. Monoclonal antibody mAb#4 is a preferred immunotherapy agent.

A method of inhibiting growth in vitro of bacteria, such as a xanthomonad or a mycobacterium, comprises the steps of providing an immunological agent capable of inhibiting the activity of a chorionic gonadotropin-like protein produced by the bacteria and contacting the bacteria with the immunological agent.

DETAILED DESCRIPTION OF THE INVENTION

Figure 1:
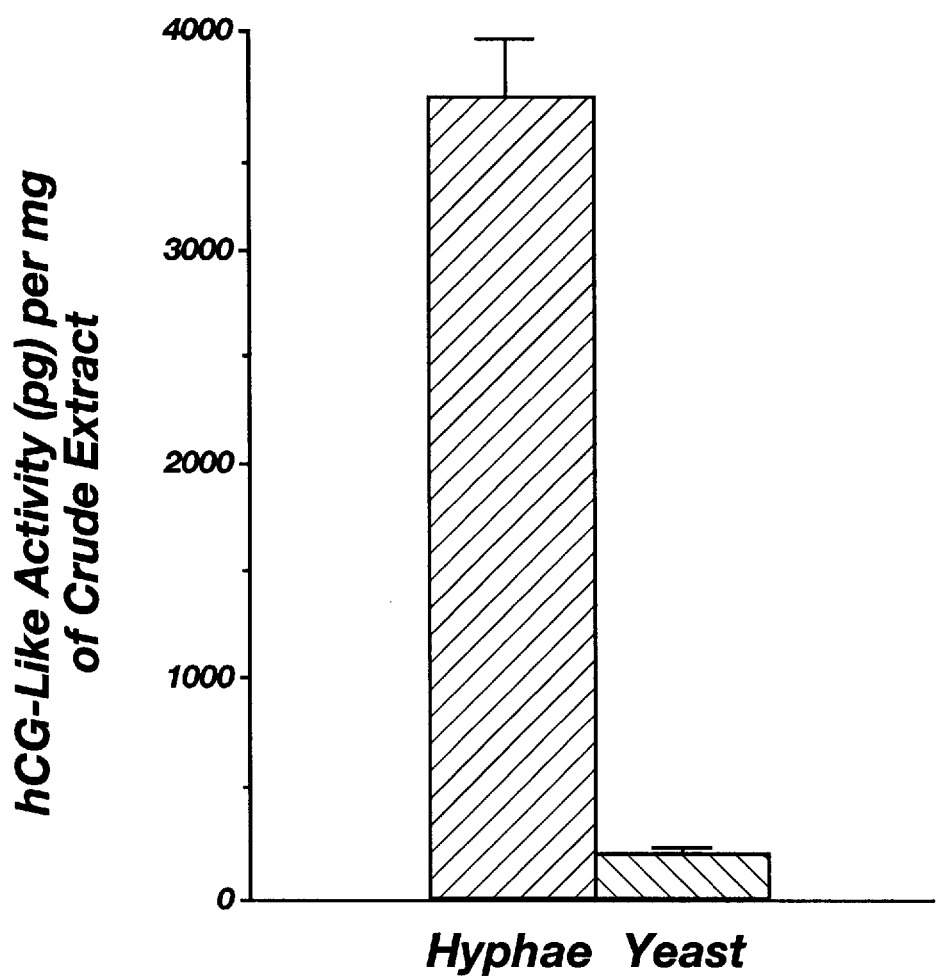
FIG. 1 is a bar graph showing the relative amounts of CG-like protein in hyphal and yeast forms of *Candida albicans*.

Before the present method of controlling growth of microorganisms by modulation of chorionic gonadotropin-related protein activity is disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the content clearly dictates otherwise. Thus, for example, reference to a method of controlling infectious microorganisms by delivering "an immunotherapy agent" includes a mixture of two or more immunotherapy agents, reference to "an epitope" includes reference to one or more of such epitopes, and reference to "a peptide" includes reference to a mixture of two or more peptides.

In describing and claiming the present invention, the following terminology will be used in accordance with the definitions set out below.

As used herein, "chorionic gonadotropin-like protein" or "CG-like protein" is a protein expressed in a species other than the human species that exhibits immuno-cross reactivity to human chorionic gonadotropin.

As used herein, "warm-blooded animal" includes the human species.

As used herein, "transition" means the change in growth habit of Candida from the blastospore to hyphal form.

As used herein, "immunotherapy agent" means a monoclonal antibody, polyclonal antiserum, purified immunoglobulin, or the like or a fragment or mixtures thereof capable of binding and inhibiting the activity of a selected CG-like protein. The binding and inhibitory effect of the immunotherapy agent on the CG-like protein can be in vitro and/or in vivo.

An "effective amount" of an immunotherapy agent is an amount, as is routinely determined by persons skilled in the art, that neutralizes the activity of a selected antigen, such as the activity of a CG-like protein. An "effective amount" of an antigen, such as a CG-like protein, is an amount necessary to be delivered to a warm-blooded animal for producing a neutralizing immune response to the antigen. An "effective amount" of a peptide delivered to a warm-blooded animal for blocking a receptor of an autoregulatory CG-like protein is an amount necessary to produce the intended result. The quantity that constitutes an "effective amount" may vary depending on the agent being administered, the species of warm-blooded animal in which infection is being controlled, the CG-like protein being neutralized, the species of infectious microorganism, and other factors, and will be limited only by functionality.

Candida albicans Transition

Yeast cultures of *C. albicans* (F16 strain, Associated Regional University Pathologists, Salt Lake City, Utah) were prepared by subculturing from a stock culture in liquid media enriched with 12.6 g of synthetic complete powder (597 mg of each of uracil, L-histidine HCL, L-arginine, and L-methionine; 896 mg of each of L-leucine, L-isoleucine, and L-lysine HCl; 1.493 g L-phenylalanine; 2.985 g L-glutamic acid; 4.478 g L-valine; 11.194 g L-serine; 19.98 g tryptophan, 19.98 g adenine; 29.97 g tyrosine; 199.15 mg threonine; 99.97 g aspartate; and 19.99 g glucose; all obtained from Sigma Chemical Co., St. Louis, Mo.) and 200 g yeast nitrogen base without amino acids (Difco Laboratories, Detroit, Mich.) per liter of double distilled water.

Yeast cells were counted using a hemacytometer, and $10^8$ blastospores per ml of growth media were incubated for 4 hours at 37° C. in media without or with various antibodies at a final titer of 1:200. The yeast cells were then centrifuged at 1000 g, recounted, and resuspended at a final concentration of $5 \times 10^5$ blastospores per ml of horse serum (Hyclone Labs, Logan, Utah). Exposure to serum induces transition. Antibodies were added to the horse serum at a final titer of 1:400, and the petri dishes were then incubated at 37° C. for 24 hours. After the incubation period, hyphal formation was observed directly using an inverted tissue culture microscope (Olympus IMT) and the percentage of germination was assessed with a hemacytometer. All germ tubes that developed a length equal to or greater than the width of the blastospore were counted as positive for transition. Three independent transition experiments were performed.

Mouse monoclonal antibodies (mAb) used were all developed in house and have been described in earlier publications, which are hereby incorporated by reference, as identified below. Antibody mAb#4 is an immunoglobulin $G_1$ (IgG$_1$) that reacts with both intact hCG and isolated β-subunit of hCG, but does not react with the free α-subunit of hCG, intact hLH, or the free carboxy-tail of hCG, and appears to be directed toward an hCG-specific epitope on the body of βhCG-subunit. J. Griffin & W. D. Odell, *Ultrasensitive immunoradiometric assay for chorionic gonadotropin which does not react with luteinizing hormone nor free beta-chain of hCG and which detects hCG in blood of nonpregnant humans,* 103 J. Immunol. Methods 275 (1987). The percentage of cross-reactivity of mAb#4 with CaCGLP calculated at a 50% B/B$_0$ is 6.9%. O. Caticha et al., *Characterization of a human chorionic gonadotropin-like protein from Candida albicans,* 132 Endocrinology 667 (1993). Antibody mAb#9 is also an IgG$_1$ and does not react with the free α or β-subunit of hCG, but does react with the intact hCG molecule and intact hLH. This antibody is thought to be directed against epitopes of intact hCG shared by hLH. J. Griffin & W. D. Odell, *Ultrasensitive immunoradiometric assay for chorionic gonadotropin which does not react with luteinizing hormone nor free beta-chain of hCG and which detects hCG in blood of nonpregnant humans,* 103 J. Immunol. Methods 275 (1987). The percentage of cross-reactivity of mAB#9 with CaCGLP at a 50% B/B$_0$ is 2.5%. O. Caticha et al., *Characterization of a human chorionic gonadotropin-like protein from Candida albicans,* 132 Endocrinology 667 (1993). Antibody mAb#α-chain is an anti-α-chain antibody that shows a 1.6% cross-reaction with intact hCG, about 1% cross-reaction with intact hLH, hFSH, and hTSH, a 4.4% cross-reaction with CaCGLP, and no cross-reaction with the free β-subunit of hCG. O. Caticha et al., *Characterization of a human chorionic gonadotropin-like protein from Candida albicans,* 132 Endocrinology 667 (1993); S. Grover et al., *Ultrasensitive, specific, two-antibody immunoradiometric assay that detects free alpha subunits of glycoprotein hormones in blood of nonpregnant humans,* 37 Clin. Chem. 2069 (1991). Antibody mAb#121 shows reaction with the β-subunit of hCG and intact hCG, but no reaction with hLH, hFSH, hTSH, α-subunits of the pituitary glycoproteins or CaCGLP. O. Caticha et al., *Characterization of a human chorionic gonadotropin-like protein from Candida albicans,* 132 Endocrinology 667 (1993); J. Griffin & W. D. Odell, *Ultrasensitive immunoradiometric assay for chorionic gonadotropin which does not react with luteinizing hormone nor free beta-chain of hCG and which detects hCG in blood of nonpregnant humans,* 103 J. Immunol. Methods 275 (1987). Antibody mAb#21 reacts specifically with intact hTSH and does not cross-react with hLH, hFSH, hCG, or with CaCGLP. W. Odell et al., *Two-monoclonal-antibody sandwich-type assay for thyrotropin, with use of an avidin-biotin separation technique,* 32 Clin. Chem. 1873 (1986). All of the monoclonal antibodies described above had an initial concentration of 1 mg/ml. The only polyclonal antiserum used was a rabbit anti-hCG (pAb#SLO), produced by standard methods, that reacts equally well with intact hCG, hLH, and the isolated β-subunit of hCG. The percentage of cross-reactivity with CaCGLP is approximately 0.125%.

Under the conditions used in the transition assay, control cultures showed complete transition to long hyphae and mycelium. The presence in the growth medium of antibodies pAb#SLO, mAb#9, mAb#121, mAb#21, and mAb#α-subunit did not alter this transition. Addition of mAb#4 to the growth medium, however, resulted in inhibition of hyphal and germ tube formation. Clusters of yeast cells were visible with fewer than 5% showing germ tubes.

Immunocytochemistry of Candida albicans

One milliliter of *C. albicans* blastospores in stationary phase or 5 ml of horse serum containing hyphae were washed three times in distilled water and resuspended in 1 ml of distilled water. Slides treated with "VECTABOND"

(Vector Labs, Burlingame, Calif.) were circled with Pap pen (Kiyota Int., Elk Grove Village, Ill.) and a drop of the mixture containing yeast or hyphae was applied. The slides were then dried at room temperature and fixed with acetone for 10 min at room temperature. Staining for CaCGLP was performed using minor modifications of the avidin-biotin-horseradish peroxidase technique, S. Hsu et al., *Use of avidin-biotin-peroxidase complex (ABC) in immunoperoxidase techniques: a comparison between ABC and unlabeled antibody (PAP) procedures,* 29 J. Histochem. Cytochem. 577 (1981), as described in the "VECTASTAIN" (Vector Labs, Burlingame, Calif.) avidin-biotin-horseradish peroxidase kit immunohistochemical detection system. These modifications were as follows. The endogenous peroxidase was quenched with 2% $H_2O_2$ in methanol (Baxter, Deerfield, Ill.) for 15 minutes at room temperature, then blocked with 3% normal goat serum, 1% casein, 0.3% Triton X-100, 1% bovine serum albumin, 0.5M NaCl, and 0.1M Tris.HCl, pH 7.4, for 30 min at 37° C. $H_2O_2$, Triton X-100, bovine serum albumin, NaCl, and Tris.HCl were obtained from Sigma Chemical Co. The primary antibody was mAb#4 or mouse non-immune IgG (negative control; supplied at 1 mg/ml by Sigma Chemical Co.), diluted 1:250 in 1.5% normal goat serum, 0.5% casein, 0.3% Triton X-100, 0.5% bovine serum albumin, 0.3M NaCl, and 0.1M Tris.HCl, pH 7.4, and incubated for 45 min at 37° C. The secondary antibody, biotinylated goat anti-mouse IgG (supplied at 1 mg/ml by Sigma Chemical Co.), was applied at 1:200 dilution in the same solution as the primary antibody, and incubated for 45 minutes at 37° C. Immunoreactivity was revealed by an avidin-biotin-horseradish peroxidase complex using the peroxidase substrate, 3,3'-diaminobenzidine. When a satisfactory brown color signal was obtained, the slides were washed, counterstained with aqueous hematoxylin (Biomeda Corp., Foster City, Calif.) and dehydrated in graded ethanol washes. After a final wash in "AMERI-CLEAR" (Baxter) the slides were mounted using a "PER-MOUNT" (Fisher Scientific, Fair Lawn, N.J.) solution.

Blastospores of *C. albicans* showed no reactivity with mAb#4, while hyphal forms strongly reacted. No reactivity was observed in either yeast or hyphal forms with the negative controls using mouse IgG.

To ensure that no gonadotropin present in the horse serum was influencing results, control studies were performed without horse serum. In these studies, transition was caused by exposure of blastospores to acid plain media (pH 3.5). This method of inducing transition is not as efficient as exposure to horse serum. Hyphae produced by exposure to low pH, however, also stained with anti-hCG antibodies, while yeast forms showed no immuno-staining. Thus, antibody mAb#4 binds to the infective hyphal form of *C. albicans*, but shows no reactions with non-infective yeast forms. Immunocytochemical staining of hyphae has also been observed with a polyclonal anti-hCG antibody, but only mAb#4 inhibited transition in vitro and prevented infection in vivo (shown below). Thus, mAb#4 appears to bind an epitope on CaCGLP that is important in controlling transition. In separate studies, mAb#4 did not directly bind to the *C. albicans* hCG receptor, and thus mAb#4 does not act directly on the receptor to prevent ligand binding.

CaCGLP Activity in Crude Extracts of Yeast and Hyphae

Despite not being able to detect the presence of CaCGLP by immunostaining, other evidence suggested that small amounts of CaCGLP were present in blastospores. CaCGLP was extracted and measured from large volumes of blastospores and compared to amounts extracted and measured from hyphae according to the methods described in O. Caticha et al., *Characterization of a Human Chorionic Gonadotropin-like Protein from Candida albicans,* 132 Endocrinology 667 (1993). These results are summarized in FIG. 1, wherein it is shown that hyphae contain about 17.5 times more CaCGLP than the yeast form of the fungus. These results also further support the involvement of CaCGLP in transition of *C. albicans* from yeast to hyphal form.

Control of *Candida albicans* In Vivo

Six week old male BALB-C mice were used for these experiments. In the first experiment (Table 1), 7 animals were used per group; in the second experiment (Table 2), 10 animals per group were used. *C. albicans* ($10^8$ organisms/ml) pre-incubated in synthetic media without antibodies or in synthetic media containing mAb#4 or mAb#21, were injected via tail vein ($10^7$ organisms/animal). All antibodies were present at a final titer of 1:400. After 24 hours, the animals were sacrificed and their kidneys removed for histological studies (right kidneys), or weighed, homogenized, and used for colony counts on yeast peptone dextrose (YPD) plates (left kidneys). YPD plates contained 20 g Bacto tryptone (Difco), 10 g yeast extract (Difco), 15 g Agar select (Sigma), and 20 g D-glucose (Sigma) per liter of double distilled water. If the plates after incubation contained too many colonies to be counted, dilutions were made and the number of colonies per gram of kidney tissue was estimated. Control animals not receiving the yeast injections showed no *C. albicans* growth under the same experimental conditions, indicating that spontaneous Candida infections were not present.

Data were analyzed using the non-parametric Kruskal-Wallis test to compare the different number of colonies per kidney obtained in all groups. A Wilcoxon rank-sum test was performed for all pairs to identify the specific differences between the groups. P values less than or equal to 0.05 were considered significant for two-tailed analysis using Statistix 3.0, an interactive statistical analysis program for microcomputers from Analytical Software (Tallahassee, Fla.).

The effects of incubation of *C. albicans* yeast with mAb#4 on infectivity in vivo are illustrated in Tables 1 and 2. In both experiments the Kruskal-Wallis test was significant (p<0.004). The Wilcoxon rank-sum test located the differences, and in both instances the group treated with mAb#4 was the one with the fewest colony counts. Control groups in which *C. albicans* was incubated without any antibody or with an anti-TSH monoclonal (mAb#21), showed no difference in either experiment.

TABLE 1

| | Colonies per gram of kidney[a,b] | | |
|---|---|---|---|
| Animal no. | mAb#4 | mAb#21 | No antibody |
| 1A | 0 | 7556 | 8553 |
| 2A | 83 | 4886 | 3370 |
| 3A | 0 | 8587 | 1733 |
| 4A | 537 | 3625 | 2682 |
| 5A | 0 | 18 | 2067 |
| 6A | 33 | 3170 | 2648 |
| 7A | 22 | 3890 | 9302 |

[a]Kruskal-Wallis: p = 0.0034
[b]Wilcoxon (two-tailed): mAb#4 × mAb#21, p = 0.007; mAb#4 × no antibody, p = 0.0006; mAb#21 × no antibody, p = 0.6724.

TABLE 2

| | Colonies per gram kidney[a,b] | | |
|---|---|---|---|
| Animal No. | mAb#4 | mAb#21 | No antibody |
| 1B | 7245 | 8604 | 9271 |
| 2B | 489 | 9213 | 10894 |
| 3B | 314 | 8830 | 9652 |
| 4B | 48 | 1482 | 3516 |
| 5B | 283 | 2870 | 2090 |
| 6B | 2927 | 3304 | 4981 |
| 7B | 0 | 9204 | 2296 |
| 8B | 264 | 5456 | 8020 |
| 9B | 2894 | 2042 | 4400 |
| 10B | 98 | 3064 | 2843 |

[a]Kruskal-Wallis: p = 0.0035
[b]Wilcoxon (two-tailed): mAb#4 × mAb#21, p = 0.0028; mAb#4 × no antibody, p = 0.0028; mAb#21 × no antibody, p = 1.0

Histological evaluation of the kidneys also showed striking differences between animals treated with mAb#4 and animals treated with mAb#21 or with no antibody. Candida infection was strikingly decreased in the kidneys of animals when the inoculum had been pretreated with mAb#4.

These studies demonstrate that one monoclonal anti-hCG antibody, mAb#4, strikingly inhibits transition of *C. albicans* in vitro, and inhibits infection in vivo. These data show that blocking of the activity of the transition stimulator, CaCGLP, prevents hyphal formation and inhibits invasiveness and infection. Although the in vivo experiments were conducted in a mouse model, the results are considered transferable to humans.

Control of Growth of *X. maltophilia*

The effect of mAb#4 and a polyclonal antiserum against xCG (pAb#xCG), prepared by standard methods, on the growth of *X. maltophilia* was tested by growing bacteria with or without the antibody and then monitoring growth by optical density at 595 nm. *X. maltophilia* (ATCC 16367) was obtained in lyophilized form and stored at 4° C. for less than 2 months before use. Bacteria were prepared fresh for each study by reconstituting one vial with 0.5 ml of trypticase soy broth (TSB) purchased from Baxter Diagnostics, Inc. (McGaw Park, Ill.). After reconstitution, the vial was incubated at 30° C. for 2 hours, then plated for isolation on an Earl's Martin Balanced (EMB) agar plate and incubated overnight at 30° C. Five to 10 small colonies were removed from the EMB plate and placed in 5.0 ml TSB, then incubated for 4–6 hours at 30° C. The bacterial preparation was used immediately as stock for growth assays. Since *X. maltophilia* produces an Fc binding protein, S. Grover et al., *Isolation of a 30 kDa mmunoglobulin Biding Protein from Pseudomonas maltophilia*, 141 J. Immunol. Methods 187 (1991), these immunoglobulin binding sites are saturated with excess purified $Fc_\gamma$ prior to addition of immunoglobulins being tested for ability to modulate growth.

Figure 2:
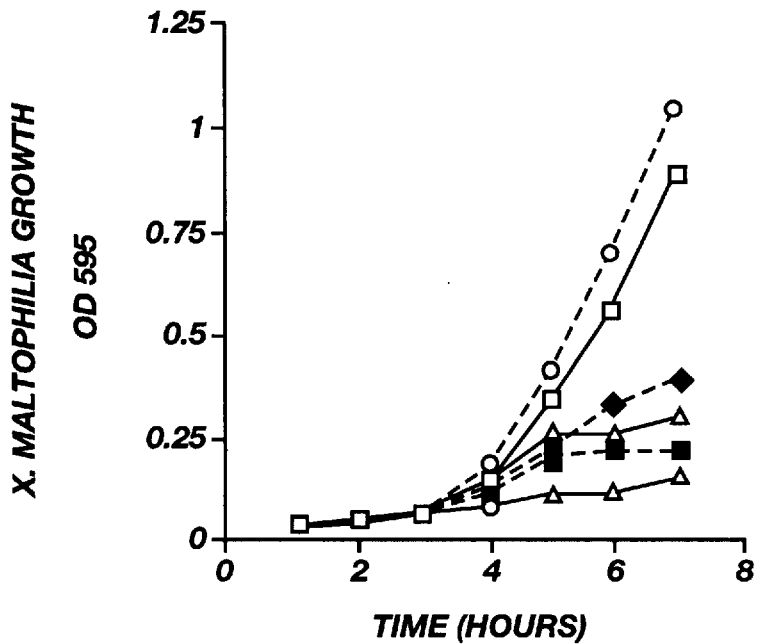
FIG. 2 is a graph showing inhibition of growth of *X. maltophilia* in the presence of the following antibodies: □ - no antibody added; ◇ - mAb#4 (monoclonal anti-hCG, 1:100 dilution); ○ - pAb#xCG (polyclonal anti-xCG, 1:100 dilution); Δ - pAb#xCG (1:1000 dilution); ■ - pAb#xCG (1:10,000 dilution); ♦ - pAb#xCG (1:30,000 dilution).

One hundred microliters of stock bacteria was added to 4.0 ml TSB in sterile 15-ml polystyrene conical centrifuge tubes. Five tubes were prepared for each antibody to be analyzed and as controls without any supplementation. One hundred microliter aliquots were removed hourly for an optical density reading at 595 nm. The results of this study, FIG. 2, shows that mAb#4, a monoclonal antibody against hCG, is effective in inhibiting growth of the bacterial culture. Further, the anti-xCG polyclonal antiserum, pAb#xCG, was effective, although not as effective as mAb#4, in inhibiting bacterial growth at titers of 1:1000, 1:10,000, and 1:30,000, but not at a titer of 1:100.

Figure 3:
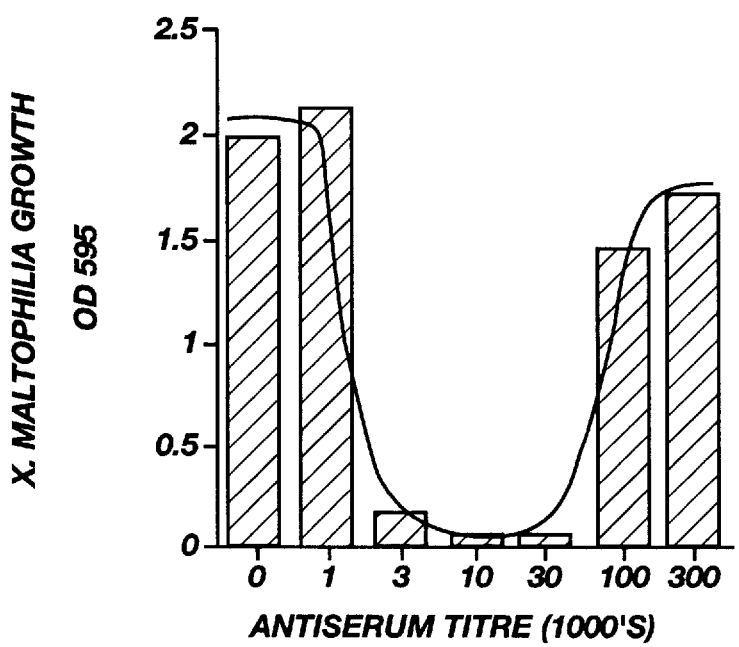
FIG. 3 is a bar diagram showing a biphasic dose response curve of growth inhibition of *X. maltophilia* to anti-xCG antiserum (pAb#xCG).

The dose response of pAb#xCG in inhibiting growth of cultures of *X. maltophilia* was further explored in the experiment summarized in FIG. 3. The bacteria were grown in TSB in the presence of various titers of the anti-xCG antiserum. The optical density at 595 nm of each culture was then determined and plotted on a bar diagram. FIG. 3 shows that there is a biphasic dose response curve of inhibition for polyclonal antiserum pAb#xCG and that an effective amount of neutralizing antibody can easily be determined by those skilled in the art.

Figure 4:
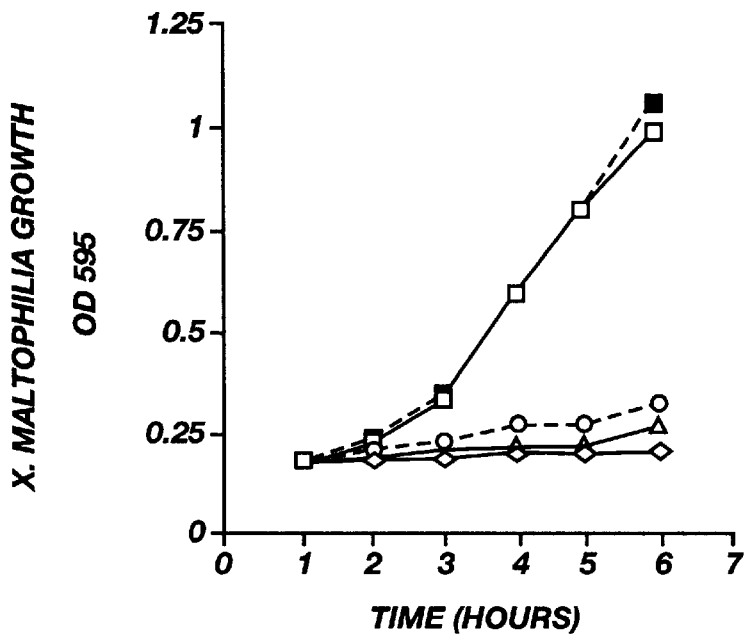
FIG. 4 is a graph showing inhibition of growth of *X. maltophilia* in the presence of the following antibodies: □ - no antibody added; ■ - mAb#21 (monoclonal anti-TSH); ○ - pAb#SLO (polyclonal anti-hCG); Δ - pAb#xCG (polyclonal anti-xCG); ◇ - mAb#4 (monoclonal anti-hCG).
Figure 5:
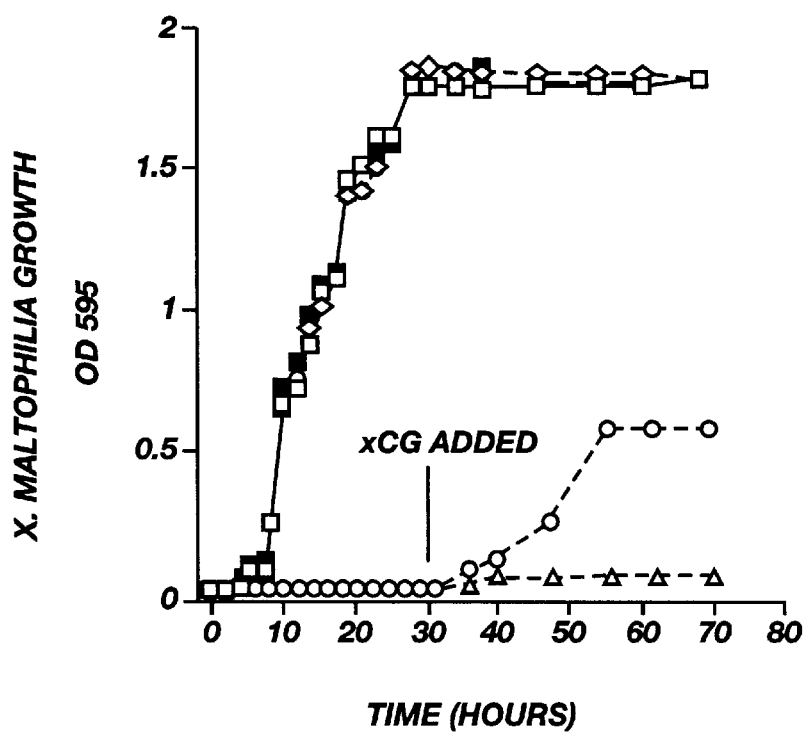
FIG. 5 is a graph showing inhibition of growth of *X. maltophilia* in a glucose-containing minimal medium by an anti-xCG antibody, and then stimulation of growth after addition of an excess of xCG at 30 hours. The antibodies added were: □ - no antibody added; ■ - NRS; ○ - pAb#xCG (polyclonal anti-xCG)+xCG; Δ - pAb#xCG (polyclonal anti-xCG); ◇ - mAb#21 (monoclonal anti-TSH).
Figure 6:
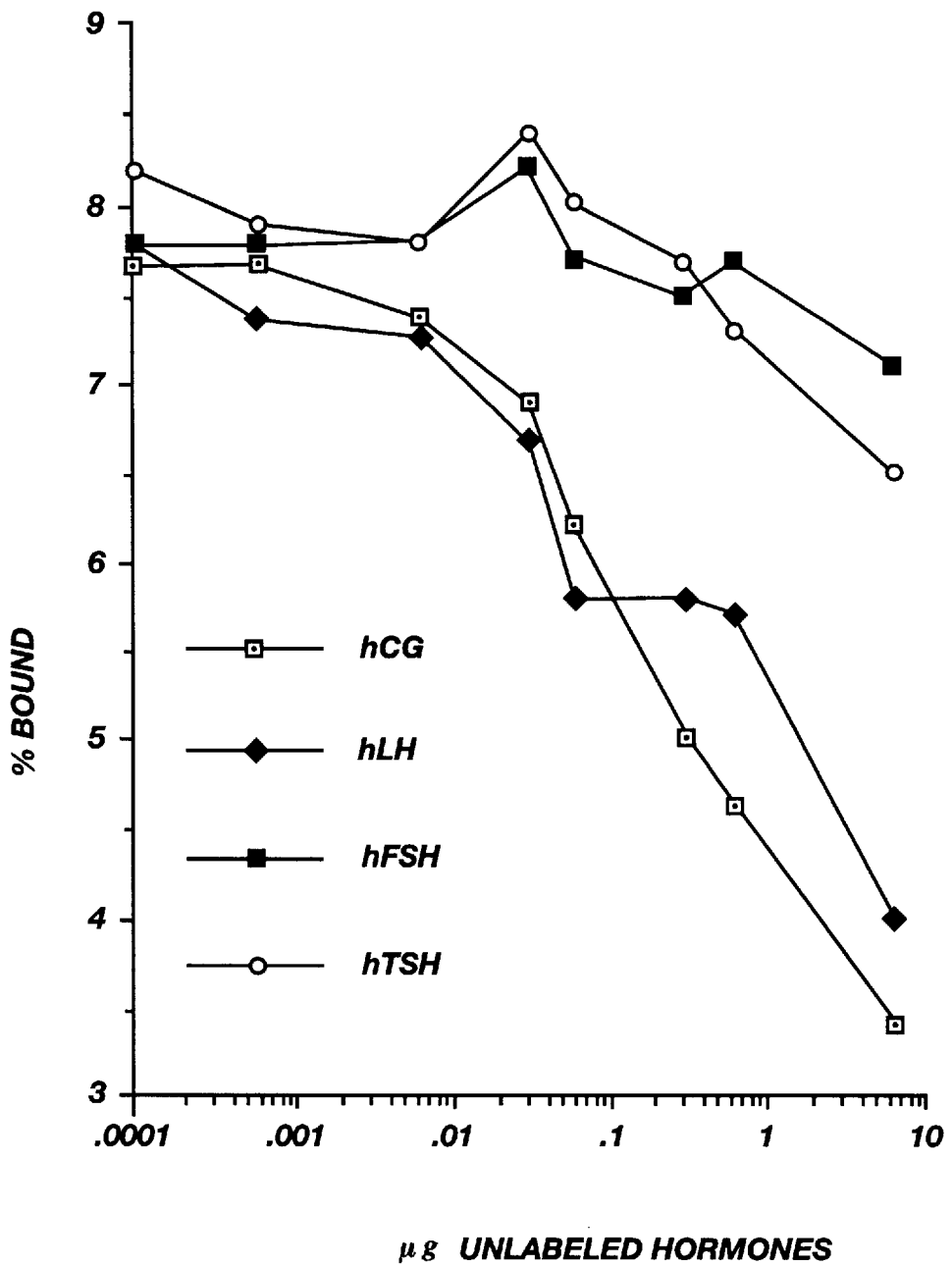
FIG. 6 is a graph showing results of a competitive displacement experiment demonstrating the presence of a CG-like protein binding site or receptor in *Mycobacterium vaccae*.
Figure 7:
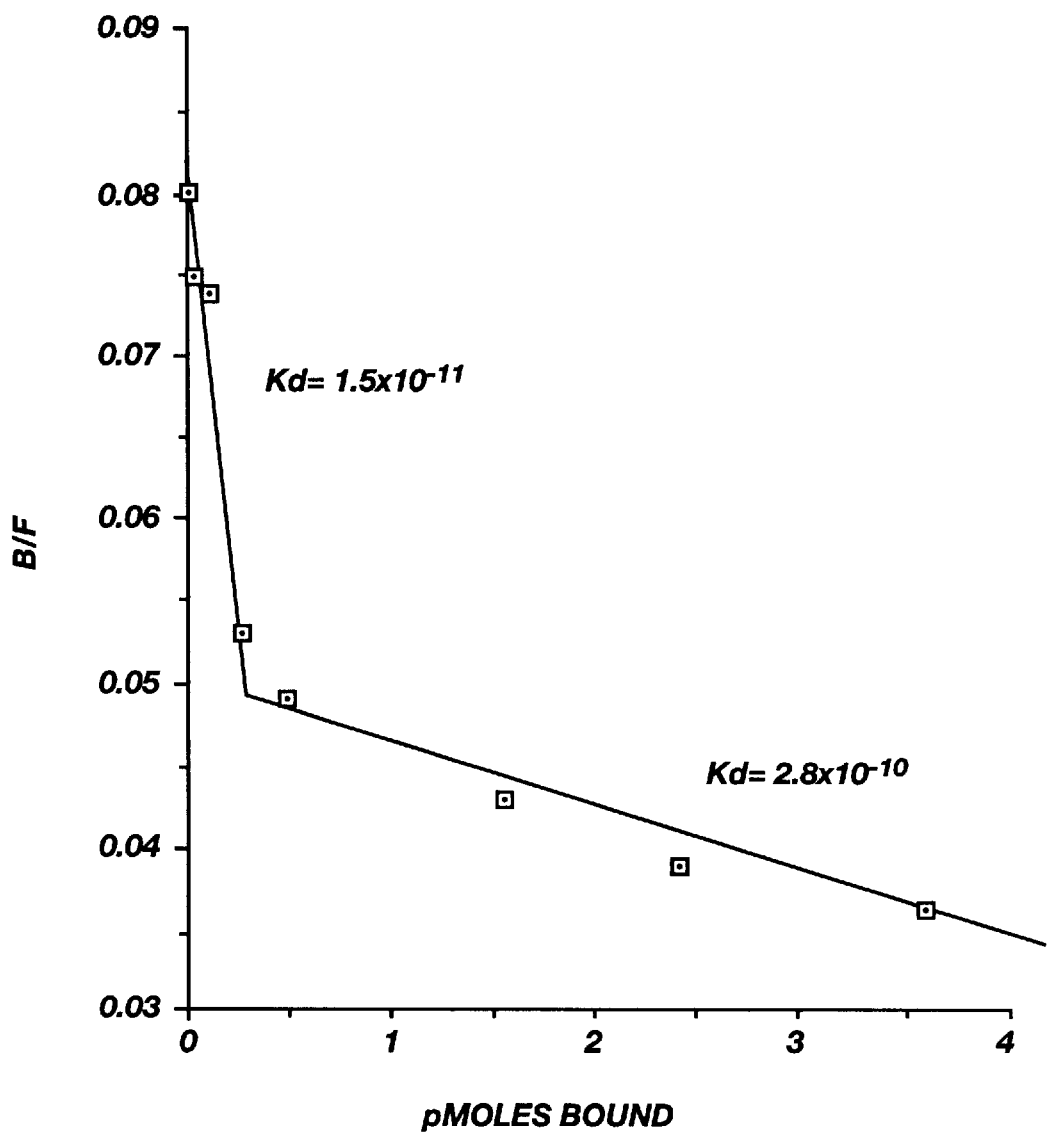
FIG. 7 is a Scatchard plot demonstrating the presence of a CG-like protein binding site or receptor in *Mycobacterium vaccae*.
Figure 8A:
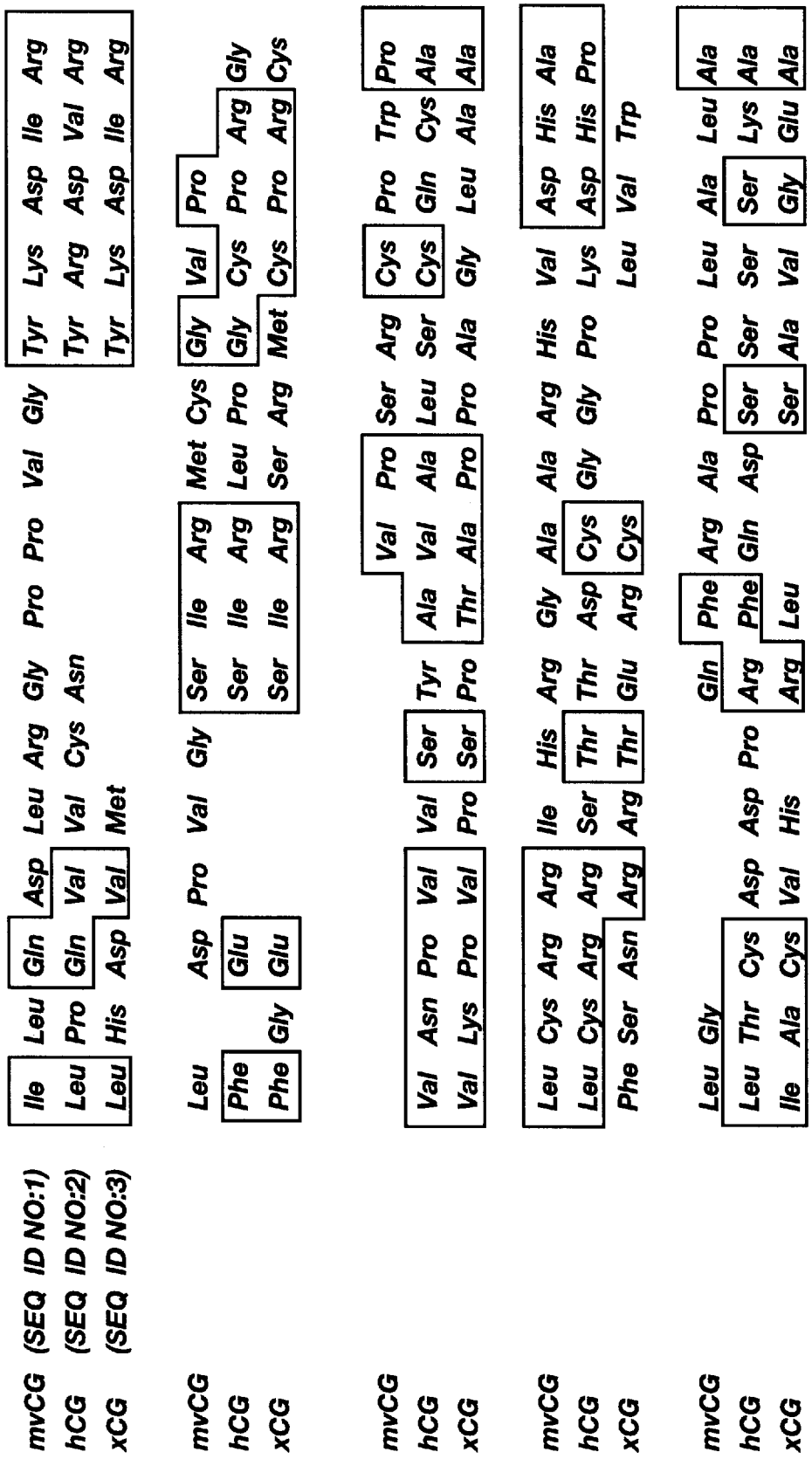
FIGS. 8A and 8B show alignment of amino acid sequences from hCG and CG-like proteins from *Xanthomonas maltophilia* and *Mycobacterium vaccae*.
Figure 8B:
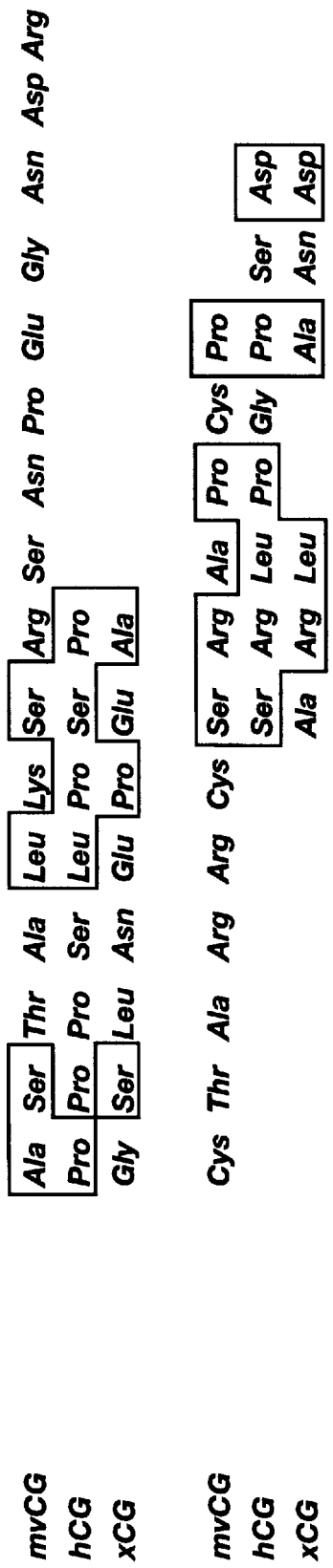

FIG. 4 shows the results of a growth inhibition experiment containing an additional anti-hCG polyclonal antiserum and a monoclonal anti-TSH antibody. The results clearly show that a specific antibody/antigen reaction is responsible for the inhibition in growth, wherein a monoclonal anti-hCG antibody (◇ - mAb#4), a polyclonal anti-hCG antiserum (○ - pAb#SLO), and a polyclonal anti-xCG antiserum (Δ - pAb#xCG) were effective inhibitors of growth, but an anti-TSH monoclonal antibody (■ - mAb#21) was not. Therefore, treatment of *X. maltophilia* with an antibody capable of binding its CG-like protein effectively inhibits growth of the bacteria. These results suggest that organisms having CG-like growth-regulating proteins can be controlled by interfering with the activity of the CG-like protein. Exposure to antibodies against the CG-like protein has been shown to be one such effective method of interfering with the activity of the CG-like protein.

FIG. 5 shows the results of an experiment in which growth of *X. maltophilia* was inhibited with a polyclonal anti-xCG antiserum (pAb#xCG) for 30 hours, and then excess xCG was added in an attempt to cause initiation of growth. After a lag of 4–8 hours, growth commenced while other cultures maintained in the continued presence of the anti-xCG antibody failed to grow. The medium for these experiments was minimal essential medium (MEM) with glucose, J. Miller, Experiments in Molecular Genetics, Cold Spring Harbor Laboratory, Cold Spring Harbor, N.Y. (1972), as the only carbon and energy source. It is generally believed by bacteriologists that bacterial growth occurs in a log dose response phase, because after sustained growth the energy source becomes limiting and growth slows and then ceases. In the instant experiment, an energy source (glucose) was present throughout the period when growth was inhibited by anti-xCG antibodies. This experiment demonstrates that an excess of a CG-like protein can stimulate growth provided a carbon and energy source is present.

Control of Growth of Mycobacteria

A rise in the incidence of tuberculosis (TB) has become evident recently, due at least in part to the increasing numbers of immunocompromised individuals in the population and an increase in drug resistance by the etiological agents of TB, e.g., *Mycobacterium tuberculosis.* Since interfering with CG-like growth-regulating proteins of microorganisms is a new approach to control of microorganisms, experiments were conducted to test the effectiveness of this strategy against a mycobacterium.

Using methods identical to those used in studies on *X. maltophilia,* D. Carrell & W. Odell, *A bacterial binding site which binds human chorionic gonadotropin but not hunan luteinizing hormone,* 18 Endocrine Res. 51 (1992), incorporated herein by reference, experiments were conducted to determine whether a binding site for hCG was present in a species that does not infect humans, *M. vaccae* (ATCC 15483). This species grows slowly on MEM, with glucose as the only energy substrate, and reached mid log phase at about 60 hours. A high affinity binding site ($K_d=10^{-11}$) was identified, as shown in FIGS. 6 and 7. FIG. 6 shows the results of competitive displacement of $^{125}$I-hCG binding to *M. vaccae.* Both hCG and hLH display competitive binding with high affinity. FIG. 7 shows a Scatchard plot of binding of hCG to *M. vaccae.*

Based on the presence of a high affinity binding site for hCG in *M. vaccae,* an endogenous CG-like protein was postulated to be produced by this bacterium. Using the nucleotide sequence of the xCG gene, polymerase chain reaction (PCR) primers, identified herein as SEQ ID NO:4 and SEQ ID NO:5, were designed for amplifying DNA isolated from *M. vaccae.* A 485 bp DNA was produced upon PCR amplification with these primers. The nucleotide sequence of this amplified *M. vaccae* DNA was determined, representing a partial sequence of a *M. vaccae* gene homologous to the xCG gene. These data are consistent with the presence of a *Mycobacterium vaccae* chorionic gonadotropin-like protein (mvCG) and receptor in mycobacteria. FIG. 8 shows an amino acid alignment of mvCG (SEQ ID NO:1), hCG (SEQ ID NO:2), and xCG (SEQ ID NO:3).

Figure 9:
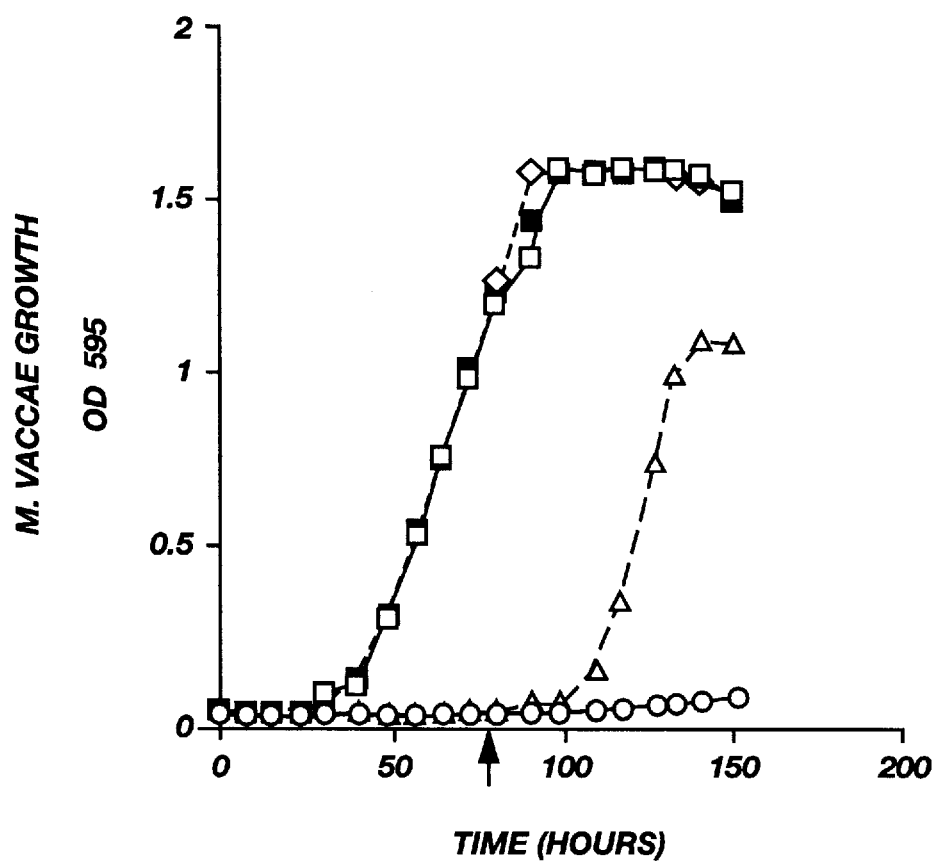
FIG. 9 is a graph showing inhibition of growth of *Mycobacterium vaccae* in the presence of the following antibodies: □ - no antibody added; ◇ - mAb (monoclonal antihuman TSH); ○ - pAb#xCG (polyclonal anti-xCG, 1:10,000 dilution); Δ - pAb#xCG+xCG (1:10,000 dilution; excess sCG was added at 70 hours as indicated by the arrow); ■ - NRS (normal rabbit serum).

An experiment was conducted to test whether antibodies against a CG-like protein can inhibit growth of a mycobacterium. FIG. 9 shows that polyclonal anti-xCG antiserum (○; pAb#xCG) is effective in inhibiting growth of *M. vaccae,* whereas a monoclonal anti-human TSH (◊) and normal rabbit serum (■) exhibited little or no growth inhibition. Addition of excess xCG at 70 hours (arrow) resulted in initiation of growth after a lag perior of about 30 hours. In other experiments, it has been shown that an anti-hCG monoclonal antibody (mAb#4) also inhibited growth of *M. vaccae.* Thus, interference with the activity of CG-like proteins is effective in controlling growth of mycobacteria in vitro.

In Vivo Control of Microorganisms

Control of infectious microorganisms having CG-like growth-regulating proteins can be achieved in at least three ways. First, an effective amount of an immunotherapy agent that interferes with the CG-like protein can be delivered by systemic administration into a warm-blooded animal infected with such a disease-causing microorganism such that growth of the microorganism is inhibited, thus controlling the further spread of the microorganism. See, e.g., U.S. Pat. No. 5,242,824.

In a second control strategy, the CG-like protein can be used to immunize the warm-blooded animal such that the animal mounts a neutralizing immune response against the protein. The CG-like protein must be purified before it is used for immunization. Purification of CaCGLP, Omar Caticha et al., *Characterization of a Human Chorionic Gonadotropin-Like Protein from Candida albicans,* 132 Endocrinology 667 (1993), and xCG, Sanjeev Grover et al., *Isolation of a 48.5 KD Membrane Protein from Pseudomonas maltophilia which Exhibits Immunologic Cross-Reaction to the β Subunit of Human Chorionic Gonadotropin,* 128 Endocrinology 3096 (1991), have already been described, and are hereby incorporated herein by reference. Standard affinity methods of purification can be used for purification of CG-like proteins because of the cross reactivity of existing immunotherapy agents and CG-like proteins. An effective amount of the purified CG-like protein is systemically administered into the warm-blooded animal such that the immune system of the animal develops an immune response to the protein and neutralizes or inhibits the activity of the protein. Such an effective amount may be administered in one injection or in more than one injection over a period of time, as is known in the art. After the immune response is developed by the animal, subsequent infection by the infectious microorganism is controlled by the animal's immune system. This method is patterned after the model of injection with tetanus toxoid as an active immunizing agent against tetanus. G. Edsall, *Specific prophylaxis of tetanus,* 171 J. Am. Med. Assoc. 471 (1959).

A third control strategy for controlling such infectious microorganisms is injection of the warm-blooded animal with peptides containing epitopes that bind the receptors of the CG-like protein so that the receptors are blocked by the peptides and are rendered incapable of normally regulating the growth of the organism.

Such peptides for blocking the receptors of CG-like proteins are identified and prepared as follows. Monoclonal antibodies that inhibit growth of a particular microorganism for which blocking peptides are desired are used. Growth inhibiting monoclonal antibodies have been identified for *Candida albicans, Xanthomonas maltophilia,* and *Mycobacterium vaccae.* Monoclonal antibodies that inhibit the growth of microorganisms can be identified in the same way as these. The monoclonal antibody, mAb#4, that inhibits growth of *X. maltophilia* will be exemplified, but it should be recognized that the same method can be used for identifying blocking peptides for other microorganisms. The monoclonal antibody mAb#4 is directed against portions of the body of the β subunit of hCG lying outside of the carboxyl tail region. Endoproteinase-lys C (Boehringer Mannheim) is used according the supplier's directions to digest the hCG β subunit into peptide fragments. These fragments are fractionated by HPLC and sequenced according to the method of N. Legendre & P. T. Matsudaira, *Gel Electrophoresis,* in A Practical Guide to Protein and Peptide Purification for Microsequencing 52–66 (P. T. Matsudaira, ed., 1989). Additional fragments are prepared by proteinase digestion of hCG and separation on polyacrylamide gels. J. Sambrook et al., Molecular Cloning: A Laboratory Manual (2d ed., 1989). These fragments are subjected to Western blotting, H. Towbin et al., *Electrophoretic transfer of proteins from pollyacrylamide gels to nitrocellulose sheets: procedure and some applications,* 76 Proc. Nat'l Acad. Sci. USA 4350 (1979), with identification of fragments bound by the monoclonal antibody. Those peptides reacting with the monoclonal antibody are sequenced. Following identification of the fragment of the hCG subunit involved, the process of digestion with a proteinase, Western blotting, and sequencing is repeated using a different proteinase to yield smaller peptides. This procedure leads to identification of a sequence recognized by the blocking monoclonal antibodies. This assumes, of course, that the recognized sequence is linear. It is also possible that the epitope recognized by the monoclonal antibody is nonlinear due to the secondary or tertiary folding of the hCG subunit. From these data, oligopeptides with similar sequence are synthesized by chemical synthesis, B. Merrifield, 85 J. Am. Chem. Soc. 2149–2156 (1963); B. Merrifield et al., 21 Biochemistry 5020–31 (1982); Houghten, 82 Proc. Nat'l Acad. Sci. USA 5131–35 (1985), or biotechnological methods, J. Sambrook et al., Molecular Cloning: A Laboratory Manual (2d ed., 1989), and tested for binding to the receptor and blocking of the native xCG ligand. Several peptidomimetic inhibitors of enzymes have been described using these techniques. A. Smith et al., *Design and synthesis of peptidomimetic inhibitors of HIV-1 protease and renin: evidence for improved transport,* 37 J. Med. Chem. 215 (1994); S. Francis et al., *Molecular characterization and inhibition of a Plasmodium falciparum aspartic hemoglobinase,* 13 EMBO J. 306 (1994); A. Garcia et al., *Peptidomimetic inhibitors of Ras farnesylation and function in whole cells,* 268 J. Biol. Chem. 18415 (1993).

The peptides can be synthesized by chemical synthesis, such as with any of the peptide synthesizers that are commercially available, or by genetically engineering a microorganism, such as *E. coli,* to express the peptide.

Following chemical synthesis or expression in a microorganism, the peptide is purified according to standard methods such as gel electrophoresis and HPLC, before systemic administration of an effective amount into the warm-blooded animal. Upon infection by the infectious microorganism, the peptide is taken up by the microorganism, the peptide binds the CG-like protein's receptors, and thus growth and further infection by the infectious microorganism is inhibited.

EXAMPLE 1

Primers for PCR amplification of a gene encoding a CG-like protein in *M. tuberculosis* are designed according to methods well known in the art, as demonstrated above in designing primers (SEQ ID NO:4 and SEQ ID NO:5) for amplification of *M. vaccae* DNA encoding a CG-like protein. E.g., U.S. Pat. No. 4,965,188. *M. tuberculosis* DNA is isolated according to standard methods, e.g., J. Sambrook et al., Molecular Cloning: A Laboratory Manual (2d ed., 1989), and the gene for the *M. tuberculosis* CG-like protein (mtbCG) amplified by PCR and cloned into a high yield expression vector. E.g., U.S. Pat. No. 4,965,188; J. Sambrook et al., Molecular Cloning: A Laboratory Manual (2d ed., 1989); F. Ausubel et al., 2 Current Protocols in Molecular Biology 16.2.1–16.2.5, supp. 11(1987). The cloned mtbCG gene is then expressed in bacteria, yeast, or a similar microorganism, and the expressed protein purified. Polyclonal antisera and monoclonal antibodies against the recombinant mtbCG protein are then prepared according to standard methods. E.g., W. Odell & M. Hescox, *Large-scale production of specific antisera for radioimmunoassay of human follicle-stimulating hormone,* in Structure-activity Relationships of Protein and Polypeptide Hormones, Excerpta Medica 139–47 (M. Margoulies & F. Greenwood, eds., 1971); W. Odell et al., *Two-monoclonal-antibody "sandwich"-type assay for thyrotropin, with use of an avidin-biotin separation technique,* 32 Clin. Chem. 1873 (1986).

Modulation of growth of *M. tuberculosis* is performed as follows. The course of *M. tuberculosis* growth under controlled conditions is determined. Mid log phase organisms are exposed for at least 2 hours at 4° C. to normal rabbit serum, control polyclonal antisera or monoclonal antibodies, or polyclonal antisera or monoclonal antibodies against the mtbCG protein, and growth characteristics observed. Additional aliquots of these control immunglobulins are added at 1–2 day intervals during growth. Growth is monitored by optical density.

Example 2

Culture diagnosis of TB is performed according to standard methods, with the exception that an effective amount of mtbCG or other effective CG-like protein is added to the cultures to stimulate growth and, thus, shorten the time needed for growth of *M. tuberculosis*.

EXAMPLE 3

Monoclonal antibodies or polyclonal antisera according to Example 1 are systemically administered to a warm-blooded animal infected with *M. tuberculosis* to treat tuberculosis in such animal.

EXAMPLE 4

Peptides that occupy the mtbCG receptor and prevent binding of mtbCG in *M. tuberculosis* are determined and derived from mtbCG according to the methods described above. Such peptides are systemically administered to a warm-blooded animal infected with *M. tuberculosis* to treat tuberculosis in such animal.

Mouse anti-human chorionic gonadotropin β-subunit hybridoma #4 was deposited on Oct. 7, 1997, with the American Type Culture Collection, 10801 University Boulevard, Manassas, Va. 20110-2209 USA, and was assigned accession number HB-12416.

We claim:

1. A method of inhibiting transition of *Candida albicans* blastospores in vitro comprising the steps of (a) providing an immunotherapy agent that binds to and inhibits hyphal and germ tube formation mediated by *Candida albicans* chorionic gonadotropin-like protein; and (b) contacting the blastospores with an effective amount of said immunotherapy agent such that said immunotherapy agent binds to and inhibits said hyphal and germ tube formation mediated by said *Candida albicans* chorionic gonadotropin-like protein, thereby inhibiting transition of said blastospores.

2. The method of claim 1 wherein said immunotherapy agent comprises mAb#4 (ATCC No. HB-12416).

* * * * *